United States Patent [19]

Ishikura

[11] Patent Number: 5,041,672

[45] Date of Patent: Aug. 20, 1991

[54] PROCESS FOR PREPARING P-PHENYLENEDIAMINES

[75] Inventor: Tsukasa Ishikura, Fukuyama, Japan

[73] Assignee: Nippon Kayaku Kabushiki Kaisha, Tokyo, Japan

[21] Appl. No.: 598,630

[22] PCT Filed: Feb. 20, 1990

[86] PCT No.: PCT/JP90/00198

§ 371 Date: Oct. 16, 1990

§ 102(e) Date: Oct. 16, 1990

[87] PCT Pub. No.: WO90/09984

PCT Pub. Date: Sep. 7, 1990

[30] Foreign Application Priority Data

Feb. 21, 1989 [JP] Japan ................................. 1-39293

[51] Int. Cl.$^5$ .................. C07C 211/51; C07C 209/36

[52] U.S. Cl. .................... 564/417; 562/456; 562/458; 564/416; 564/418

[58] Field of Search .................. 564/416, 417, 418; 562/456, 458

[56] References Cited

FOREIGN PATENT DOCUMENTS 50-25555 of 1975 Japan .
54-59237 5/1979 Japan .
58-128347 7/1983 Japan .

*Primary Examiner*—Richard L. Raymond
*Attorney, Agent, or Firm*—Henry C. Nields

[57] ABSTRACT

A process for producing p-phenylenediamine or a derivative thereof which comprises reducing p-nitroaniline or a derivative thereof by hydrazine in the presence of an aromatic quinone compound or an aromatic dihydroxy compound.

5 Claims, No Drawings

PROCESS FOR PREPARING P-PHENYLENEDIAMINES

TECHNICAL FIELD

The present invention relates to a process for preparing p-phenylenediamines.

BACKGROUND ART p-Phenylenediamines are important compounds (intermediates) for use as materials for dyes, pigments, polymers and agricultural chemicals.

Phenylenediamines can be prepared by various conventional processes. For instance, as disclosed in Japanese Patent Application Laid-Open (KOKAI) No. 51-26826 (1976), o-phenylenediamine can be prepared by hydrogenation of o-nitroaniline. This process, however, involves a reaction under a high pressure and, therefore, requires special equipment and an intricate operation for separating a catalyst.

Besides, as described on page 261 of BIOS FINAL REPORT 1153, nitroaniline can be reduced by an aqueous sodium sulfide solution to phenylenediamine. However, this process has the problem that large amounts of alkaline sulfur compounds are by-produced.

Also, it is possible to reduce p-nitroaniline by iron powder to obtain p-phenylenediamine, as described in PB 85172, but this process involves difficulties in separation of the p-phenylenediamine from by-produced iron compounds and in disposal of the iron compounds by-produced in large amounts.

As disclosed in Japanese Patent Application Laid-Open (KOKAI) No. 54-59237 (1979), furthermore, p-phenylenediamine can also be obtained by reducing p-nitroaniline by hydrazine by use of an iron oxide or iron hydroxide catalyst, however, this process necessitates troublesome operations such as separation of the catalyst used.

It is further known to obtain aminoanthraquinones by reacting nitroanthraquinones with hydrazine, as disclosed in Japanese Patent Application Laid-Open (KOKAI) No. 50-25555 (1975). It has not been known, however, to reduce other nitro compounds by hydrazine in the presence of an aromatic quinone compound or an aromatic dihydroxy compound as a catalyst, as in a process according to the present invention.

The conventional processes thus have the drawbacks of the intricate operation for separating the catalyst, the disposal of needless substances which are by-produced in large amounts, the necessity for a special apparatus, and so on.

The present invention provides an industrial process by which p-phenylenediamines can be prepared in a high yield and which is free from the above-mentioned problems.

DISCLOSURE OF INVENTION

The present invention relates to a process for preparing p-phenylenediamines which comprises reducing p-nitroanilines by hydrazine in the presence of an aromatic quinone compound or an aromatic dihydroxy compound.

The present invention will now be described in more detail below.

In the present invention, p-nitroanilines are used as starting materials. Preferred examples of the starting material are the compounds represented by the following formula:

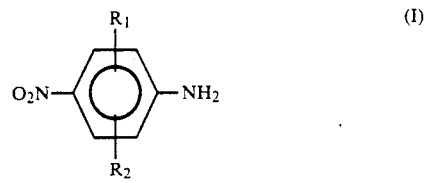

wherein $R_1$ and $R_2$ represent, independently, a hydrogen atom, a chlorine atom, a bromine atom, a fluorine atom, a methyl group, a methoxyl group, an ethoxyl group or a carboxyl group.

Specific examples of the compounds represented by the formula (I) include p-nitroanilines such as p-nitroaniline, 2-chloro-p-nitroaniline, 2,5-dichloro-p-nitroaniline, 2,6-dichloro-p-nitroaniline, 2-bromo-p-nitroaniline, 2,5-dibromo-p-nitroaniline, 2,6-dibromo-p-nitroaniline, 2-bromo-6-chloro-p-nitroaniline, 2-fluoro-p-nitroaniline, 2-methyl-p-nitroaniline, 2,3-dimethyl-p-nitroaniline, 2,5-dimethyl-p-nitroaniline, 2,6-dimethyl-p-nitroaniline, 2-chloro-5-methyl-p-nitroaniline, 2-methoxy-p-nitroaniline, 5-methoxy-p-nitroaniline, 2-chloro-5-methoxy-p-nitroaniline, 5-chloro-2-methoxy-p-nitroaniline, 2,5-dimethoxy-p-nitroaniline, 2,5-diethoxy-p-nitroaniline, 5-nitroanthranilic acid, etc.

As a reaction solvent, there may be used water, alcohols, aliphatic hydrocarbons, aromatic hydrocarbons or a mixture thereof. The alcohols include methanol, ethanol, propyl alcohol, butyl alcohol, Cellosolve, etc., whereas the aliphatic hydrocarbons include dichloroethane, tetrachloroethane, etc. The aromatic hydrocarbons include chlorobenzene, dichlorobenzene, toluene, xylene, etc.

The hydrazine is used in the form of a free base (preferably, hydrazine hydrate) or in the form of a salt (hydrazine sulfate or hydrochloride), together with, if necessary, an alkali, for example, alkali metal carbonate, alkali metal acetate or, preferably, alkali metal hydroxide (e.g., sodium hydroxide, potassium hydroxide or lithium hydroxide) or other base, for example, ammonia or mono-, di- or tri-alkanolamine. These alkalis or bases are ordinarily used in an amount of 0.1 to 10% by weight based on the reaction mixture, preferably in such an amount as to make the reaction mixture have a pH of not less than 9.

The hydrazine is preferably used in an amount of at least 1.5 moles per mole of the nitro groups. The reaction can be carried out by use of 1.5 to 5 moles of the hydrazine per mole of the nitro groups, a more preferable amount of the hydrazine being 1.6 to 3 moles. The hydrazine may either be added little by little or be added all at once.

The catalyst used in the present invention is an aromatic quinone compound or an aromatic dihydroxy compound. As the aromatic quinone compound, there may be mentioned, for example, 1,2-benzoquinone, 1,4-benzoquinone, benzoquinones having one to four alkyl groups on the nucleus thereof, benzoquinones having one to four chlorine atoms on the nucleus thereof, 1,2-naphthoquinone, 1,4-naphthoquinone, and naphthoquinones having one to four alkyl groups, one to four chlorine atoms or one to four sulfonic acid groups on the nucleus thereof. As the aromatic dihydroxy compound, there may be mentioned, for example, hydroquinone, hydroquinones having one to four alkyl groups on the nucleus thereof, hydroquinones having one to four chlorine atoms on the nucleus thereof, catechol, catechols having one to four methyl groups on the nucleus thereof, catechols having one to four chlorine atoms on the nucleus thereof, 1,2-naphthalenediol, 1,4-naphthalenediol, and 1,2- or 1,4-naphthalenediols having one to four alkyl groups, one to four chlorine atoms or one to four sulfonic acid groups on the nucleus thereof.

The amount of the catalyst used is preferably 0.01 to 10% by weight, more preferably 0.05 to 2% by weight, based on the p-nitroaniline or derivatives thereof. The reaction is carried out at a temperature of 20° to 150° C., preferably 50° to 110° C. The reaction time is usually from 10 minutes to 10 hours.

The objective product thus formed can be separated from the reaction mixture by, for instance, filtration.

The purity of the objective product can be determined easily by gas chromatography.

BEST MODE FOR CARRYING OUT THE INVENTION

The present invention will now be explained in more detail while referring to the following examples.

EXAMPLE 1

A reaction vessel was charged with 60 g of isopropyl alcohol, 50 g of water, 41.4 g of 2,5-dichloro-p-nitroaniline, 6 g of sodium hydroxide and 0.3 g of 1,4-naphthoquinone. The temperature of the mixture was controlled to be 75° to 80° C., and 22 g of an 80% solution of hydrazine hydrate in water was added dropwise to the mixture over 2 hours. After the addition, the reaction mixture was refluxed with stirring for 3 hours to complete the reaction. After cooling to 5° C., the reaction product was filtered, washed with water and dried, to give 32.2 g of 2,5-dichloro-p-phenylenediamine.

Yield: 91%
Purity determined by G.C. analysis: 99.9%

EXAMPLE 2

A reaction vessel was charged with 200 g of water, 41.4 g of pulverized 2,5-dichloro-p-nitroaniline, 6 g of sodium hydroxide, 0.3 g of 1,4-naphthoquinone and 25 g of an 80% solution of hydrazine hydrate in water. The contents of the vessel were agitated at 85° to 95° C. for 9 hours to complete the reaction. The reaction product was filtered, washed with water and dried to give 34.0 of 2,5-dichloro-p-phenylenediamine.

Yield: 96%
Purity determined by G.C. analysis: 99.6%

EXAMPLE 3

A reaction vessel was charged with 60 g of toluene, 50 g of water, 37.3 g of 5-chloro-2-methyl-p-nitroaniline, 6 g of sodium hydroxide and 0.3 g of 1,4-naphthalenediol, and then the same procedure as in Example 1 was followed, to obtain 29.4 g of 2-chloro-5-methyl-p-phenylenediamine.

Yield: 94%
Purity determined by G.C. analysis: 99.8%

EXAMPLE 4

A reaction vessel was charged with 60 g of isopropyl alcohol, 50 g of water, 37.3 g of 2-chloro-5-methyl-p-nitroaniline, 5 g of potassium hydroxide and 0.6 g of 1,2-benzoquinone, and then the same procedure as in Example 1 was followed, to obtain 28.6 g of 2-chloro-5-methyl-p-phenylenediamine.

Yield: 91%
Purity determined by G.C. analysis: 99.9%

EXAMPLES pb 5 TO 8

Reactions were carried out in the same manner as in Example 1 except that the starting materials and catalysts set forth in Table 1 were used respectively. The results are shown in Table 1.

TABLE 1

| Examples | p-Nitroanilines | Catalyst | | Yield | G.C. purity |
|---|---|---|---|---|---|
| 5 | 2-Chloro-p-NA* | 2,3-Dichloro-1,4-naphthoquinone | 1.0 g | 85% | 99.8% |
| 6 | 2,5-Dimethyl-p-NA | 1,2-Naphthoquinone-4-sulfonic acid | 1.0 g | 87% | 99.9% |
| 7 | 2,5-Dimethyoxy-p-NA | 1,4-Naphthoquinone | 1.0 g | 82% | 99.9% |
| 8 | 2-Chloro-5-methoxy-p-NA | 1,4-Naphthoquinone | 1.0 g | 92% | 99.8% |

*p-NA: p-nitroaniline

COMPARATIVE EXAMPLE 1

A reaction was carried out in the same manner as in Example 1 except that 1,4-naphthoquinone was not used. As a result, 40.3 g of 2,5-dichloro-p-nitroaniline (starting material) was only recovered.

INDUSTRIAL APPLICABILITY

By the reduction of p-nitroanilines by hydrazine in the presence of an aromatic quinone compound or an aromatic dihydroxy compound, it is possible to obtain easily the corresponding p-phenylenediamines in an industrial scale.

I claim:

1. A process for producing p-nitroaniline or a derivative thereof which comprises reducing p-nitroaniline or a derivative thereof by hydrazine in the presence of an aromatic quinone compound or an aromatic dihydroxy compound.

2. A process according to claim 1, wherein the p-phenylenediamine and the derivative thereof are represented by the following formula (I):

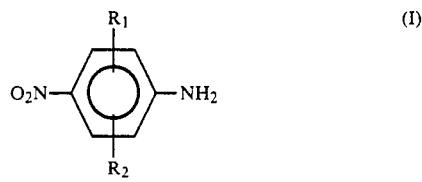

wherein $R_1$ and $R_2$ represent, independently, a hydrogen atom, a chlorine atom, a bromine atom, a fluorine atom, a methyl group, a methoxyl group, an ethoxyl group or a carboxyl group.

3. A process according to claim 1, wherein the aromatic quinone compound is 1,4-naphthoquinone or 1,2-naphthoquinone.

4. A process according to claim 1, wherein the reaction is carried out at a pH of not less than 9.

5. A process according to claim 1, wherein the p-nitroaniline derivative is 2,5-dichloro-p-nitroaniline, 5-chloro-2-methyl-p-nitroaniline or 2-chloro-5-methyl-p-nitroaniline.

* * * * *